United States Patent [19]

Baines et al.

[11] Patent Number: 4,818,535

[45] Date of Patent: Apr. 4, 1989

[54] REPELLENT COMPOSITIONS

[75] Inventors: David A. Baines, Ely; Christopher G. Faulkes, London; Andrew J. Tomlinson; Peter C. Y. K. Ning, both of Cambridge, all of England

[73] Assignee: Dalgety U.K. Limited, London, England

[21] Appl. No.: 157,368

[22] Filed: Feb. 17, 1988

[30] Foreign Application Priority Data

Feb. 18, 1987 [GB] United Kingdom ................. 8703716

[51] Int. Cl.$^4$ ........................................... A01H 25/24
[52] U.S. Cl. .................................... 424/407; 424/104; 424/405
[58] Field of Search ............... 424/403, 104, 405, 409, 424/411, 497

[56] References Cited

U.S. PATENT DOCUMENTS

| | | | |
|---|---|---|---|
| 3,846,557 | 11/1974 | Mulla et al. | 426/385 |
| 3,962,425 | 6/1976 | Oita et al. | 424/94.21 |
| 3,980,773 | 9/1976 | Oh et al. | 424/95 |
| 4,038,385 | 7/1977 | Bowyer et al. | 424/166 |
| 4,065,576 | 12/1977 | Oita et al. | 514/560 |
| 4,065,577 | 12/1977 | Oita et al. | 514/693 |
| 4,472,377 | 9/1984 | Teranishi et al. | 424/84 |
| 4,534,976 | 8/1985 | Hansen et al. | 514/169 |
| 4,656,038 | 4/1987 | Baugh | 424/164 |
| 4,657,759 | 4/1987 | Hansen et al. | 424/83 |

FOREIGN PATENT DOCUMENTS

| | | |
|---|---|---|
| 1022070 | 12/1977 | Canada . |
| 1030065 | 4/1978 | Canada . |
| 0105208 | 2/1983 | European Pat. Off. . |
| 063720 | 2/1983 | European Pat. Off. . |
| 8200039 | 7/1982 | PCT Int'l Appl. . |

OTHER PUBLICATIONS

Roger W. Bullard et al., "Evaluation of a Sunthetic Fermented Egg Coyote Attractant and Deer Repellent", *Agric. Food Chem.*, vol. 26, No. 1, 1978, pp. 160-163.

Bullard et al., "Volatile Components of Fermented Egg, an Animal Attractant and Repellent", *J. Agric. Food Chem.*, vol. 26, No. 1, 1978, pp. 165-169.

R. Teranishi et al., "Chemical Useful as Attractants and Repellents for Coyotes" *Worldwide Fuskearer Conference Proceedings*, vol. III, 1980, ed. by J. A. Chapman and D. Pursley.

"The Anal. Sac Secretion of the Red Fox . . . *Life Sciences*, vol. 14, pp. 387-400, 1974.

Egerer et al., "Preparation for and Method, for Driving Away Game From Sectors of Countryside".

Borchers et al., "The Formation and Biological Role of a Felinine *Chem. Inst*".

Primary Examiner—Thurman K. Page
Assistant Examiner—L. R. Horne
Attorney, Agent, or Firm—Hamilton, Brook, Smith & Reynolds

[57] ABSTRACT

A repellent composition e.g. for repelling deer comprises a synthetic blend of components which are characteristic of the acid fraction obtained by a Soxhlet extraction of lion faeces followed by separation into basic, neutral and acid fractions; and felinine. The composition may comprise saturated alkanoic acids with carbon atoms in the range of 3-20; saturated aliphatic alcohols with carbon atoms in the range 14-16; various compounds containing primary or secondary amino groups and having carbon atoms in the range 3-9; a fermented egg product; a bittering agent and an adhesive agent.

20 Claims, No Drawings

REPELLENT COMPOSITIONS

This invention is concerned with improvements in or relating to repellent compositions, particularly but not exclusively for repelling animals such as deer.

In for example forestry, damage by deer is a recurrent problem particularly in the case of softwood saplings.

It is an object of the present invention to provide an improved repellent composition and method.

It is known that deer have an innate fear and flight response to the aroma of lion faeces, and this occurs even when the deer have lived all their lives in territories where lions are not endemic.

This property of lion faeces can be used to repel deer from for example areas of forestry where they could otherwise cause damage, but clearly, at least in territories where lions are not endemic, it is impracticable and uneconomical to spread lion dung around the area to be protected. This difficulty could be overcome if the active constituents of the lion faeces are identified and corresponding synthetic blends of chemicals prepared.

Lion faeces comprises a complex mixture of chemicals including steroids but we have found that deer are repelled by a synthetic blend of compounds which are characteristic of the acid fraction obtained by a Soxhlet extraction of lion faeces followed by separation into basic, neutral and acid fractions: important constituents of this acid fraction are saturated alkanoic acids.

Such compounds also appear in the anal sac secretion of lions and in fox's urine.

Another animal repellent is felinine, which is a constituent of cat's urine and has the structure

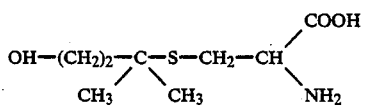

Felinine exists as L- and D-enantiomers, we believe the compound we have employed consists essentially of the L-enantiomer.

We have found that compositions comprising the blends referred to hereinabove and felinine exhibit a synergistic repellent effect.

The invention provides a repellent composition comprising (a) a synthetic blend of components which are characteristic of the acid fraction obtained by a Soxhlet extraction of lion faeces followed by a separation into basic, neutral and acid fractions; and (b) L-felinine.

The invention also provides a repellent composition comprising (a) a synthetic blend of saturated alkanoic acids with carbon atoms in the range of 3–20; and (b) felinine.

The saturated alkanoic acids may be straight or branched chain acids.

Examples of saturated alkanoic acids include:
n-propanoic acid
2-methyl propanoic acid
n-butanoic acid
2-methyl butanoic acid
3-methyl butanoic acid
n-pentanoic acid
4-methyl pentanoic acid
n-hexanoic acid
2-methyl hexanoic acid
n-heptanoic acid
n-octanoic acid
4-methyl octanoic acid
n-nonanoic acid
4-methyl Nonanoic acid
n-decanoic acid
n-undecanoic acid
n-dodecanoic acid
n-tridecanoic acid
n-tetradecanoic acid (myristic acid)
n-pentadecanoic acid
n-hexadecanoic acid (palmitic acid)
n-octadecanoic acid (stearic acid)
n-eicosanoic (arachidic acid The weight ratio of felinine to saturated alkanoic acids in a composition according to the invention can vary widely for example over the range 0.25:1 to 30:1, e.g. 10:1 to 25:1.

The invention also provides a method of repelling animals e.g. deer wherein a composition according to the invention is employed.

A composition according to the invention may comprise at least one saturated aliphatic straight or branched chain alcohol with carbon atoms in the range 6–8 e.g. 14–16; examples include n-tetradecanol; n-pentadecanol; and n-hexadecanol.

The weight ratio of $C_{14}$–$C_{16}$ saturated aliphatic alcohols to saturated alkanoic acids is for example in the range 0.02–0.05:1.

A composition according to the invention may comprise at least one aryl- (e.g. phenyl-) or substituted aryl- (e.g. hydroxyphenyl-) saturated alkanoic (e.g. acetic or propanoic) acid; examples include phenyl acetic acid and 3-phenyl propanoic acid.

A composition according to the invention may comprise any or all of pyrrolidine; piperidine; 2-pyrrolidone; 2-phenyl ethylamine; 3-methyl indole; diethylamine; n-propylamine; n-butylamine and 3-methyl butylamine each in weight ratio to saturated alkanoic acids in the composition of about 0.025:1. These compounds contain primary or secondary amino groups and have carbon atoms in the range 3–9; and compositions containing them may exhibit a particularly enhanced degree of synergism.

A composition according to the invention may comprise any of:
2-phenyl ethanol
phenol
5-amino-valeric acid
2-piperidone (γ-valerolactam)

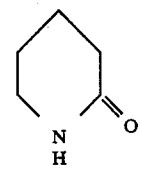

4-methyl phenol
indole
oxindole
oleic acid
linoleic acid
cholesterol
benzothiazole
2-phenoxyethanol
γ-decalactone palmitoleic acid (cis-9-hexadecenoic acid)
elaidic acid
linolenic acid
eicosenoic acid
3β-cholestanol.
5-amino-valeric acid may be regarded as a precursor of 2-piperidone.

A composition according to the invention may comprise any or all of:
3-mercapto propan-1-ol
3-(methylthio)propanol
dimethyl sulfide
dimethyl trisulfide
dimethyl tetrasulfide
N-(2-phenylethyl)acetamide
N-butyl-N-ethyl acetamide.

The acetamides can be synthesised from the corresponding amines, phenylethylamine and N-ethyl butylamine, respectively. J. March "Advanced Organic Chemistry" 3rd Edition—page 370, 1985.

A composition according to the invention may comprise a fermented egg product, which is prepared for example by the bacterial fermentation of whole chicken eggs, e.g. of the order of about 35 whole eggs per gram of saturated alkanoic acids in the composition.

Bullard et al. in J. Agric. Food Chem. Vol. 26, No. 1 1978—page 155 et seq. also describe a fermented egg product.

A composition according to the invention may comprise an agent to impart to it a bitter flavour with a view for example to counteracting any tendency for the deer in time to overcome their natural repugnance to the odour of the composition.

Bittering agents include brucine, quassin, sucrose octa-acetate, quinine, caffeine and various tannins, e.g. spray dried bark as used in the tanning industry; but we prefer to use Bitrex: denatonium benzoate, and in an amount up to for example 2% by weight of the composition.

Denatonium benzoate has the formula:

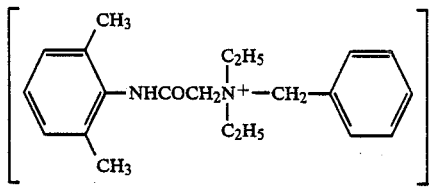

Compositions according to the invention may incorporate for example an inert carrier (e.g. a solvent or a solid excipient) for the active ingredients. The composition may for example be dispersed by spraying, spreading, diffusion or other sustained release mechanism.

One useful carrier for example, comprises an agent to impart adhesive properties to the composition so that it sticks readily to foliage and the like; examples include polybutene polymers, acrylic vinyl acetate copolymers emulsified asphaltic materials, and acrylic polymers, e.g. an adhesive aqueous acrylic emulsion which dries out on spraying and exposure to the air. We prefer to use Primal AC-33, understood to comprise 45–49% acrylic copolymer in water and in an amount e.g. 90–99% Primal by weight of the composition.

Fractionation of a Soxhlet Extraction of Lion Faeces

A method of Soxhlet extraction followed by separation into basic, neutral and acid fractions is described in relation to coyote urine by R. Teranishi et al. "Worldwide Furbearers' Conference Proceedings" Volume III (1980) pages 1839–1851 (see particularly page 1843) Editors J. A. Chapman and D. Pursley. We applied this method to lion faeces.

The lion faeces was Soxhlet extracted using 1,1,2-trichloro-trifluorethane (hereinafter "Freon") as the solvent. The extract was washed with 2% w/v sodium bicarbonate and separated into aqueous (a) and non-aqueous solvent (b) fractions.

The aqueous fraction (a) was acidified with 2M HCl and solvent extracted again with Freon to yield a solvent fraction (d) and an aqueous fraction (e); an "acid" faeces extract fraction was obtained from the solvent fraction (d).

ANALYSIS I

Acid Extract of Lion Faeces

The method of analysis was gas chromatography with flame ionisation detection, and coupled gas chromatography/mass spectrometry.

|  | % by weight |
|---|---|
| n-propanoic acid | 0.32 |
| 2-methyl propanoic acid | 2.60 |
| n-butanoic acid | 12.88 |
| 2-methyl butanoic acid | 40.95 |
| n-pentanoic acid | 2.09 |
| 4-methyl pentanoic acid | 7.37 |
| n-hexanoic acid | 1.52 |
| 2-phenyl ethanol | 0.18 |
| phenol | 6.06 |
| 2-piperidone | 0.51 |
| 4-methyl phenol | 2.04 |
| n-octanoic acid | 0.19 |
| n-decanoic acid | 0.32 |
| indole | 4.38 |
| n-dodecanoic acid | 0.20 |
| 3-phenyl propanoic acid | 14.32 |
| n-tetradecanoic acid (myristic acid) | 0.35 |
| oxindole | 0.25 |
| n-hexadecanoic acid | 1.76 |
| n-octadecanoic acid | 1.71 |
|  | 100.00 |

ANALYSIS II

Lions' Anal Sac Secretion

The method of analysis was as for the lion faeces.

|  | % by weight |
|---|---|
| n-propanoic acid | 0.84 |
| 2-methyl propanoic acid | 3.57 |
| n-butanoic acid | 0.55 |
| 3-methyl butanoic acid | 37.15 |
| 2-methyl butanoic acid | 3.49 |
| n-pentanoic acid | 1.09 |
| 2-methyl pentanoic acid | 0.61 |
| 4-methyl pentanoic acid | 0.79 |
| n-hexanoic acid | 2.14 |
| 2-methyl hexanoic acid | 3.53 |
| 4-methyl hexanoic acid | 1.49 |
| n-heptanoic acid | 1.93 |
| 2-methyl heptanoic acid | 2.58 |
| 4-methyl heptanoic acid | 0.63 |
| n-octanoic acid | 3.27 |
| 2-methyl octanoic acid | 2.50 |
| 4-methyl octanoic acid | 0.47 |
| n-nonanoic acid | 0.52 |
| n-nonanol | 0.34 |
| n-decanol | 4.23 |
| decan-2-ol | 0.59 |

-continued

| | % by weight |
|---|---|
| n-undecanol | 7.42 |
| n-dodecanol | 13.72 |
| n-tridecanol | 4.29 |
| n-tetradecanol | 1.72 |
| n-pentadecanol | 0.20 |
| n-hexadecanol | 0.34 |
| | 100.00 |

Weight ratio of $C_{14}$-$C_{16}$ saturated aliphatic alcohols to saturated alkanoic acids: 0.034:1.

Synthetic blends can be prepared corresponding precisely to Analysis I or Analysis II. However we have found that, conveniently, modifications to these recipes can be made.

SYNTHESIS OF FELININE

Crude Aqueous Solution

L-cysteine monochloride monohydrate (116 g, 0.66 moles) is added to a stored solution of concentrated hydrochloric acid (125 ml) and water (375 ml). The solution is cooled to ~0° C. and 3-methyl-3-buten-1-ol (115 g, 1.34 moles) is added dropwise to the acid solution while maintaining the temperature below 10° C.

The reaction mixture changes from colourless to white to yellow as it is allowed to warm up to room temperature, and stirring continued for 16 hours.

The yellow reaction mixture is cooled to ~0° C. and a solution of sodium hydroxide (50 g) in water (100 ml) is added dropwise while maintaining the temperature below 20° C.

The reaction mixture is extracted with diethyl ether (4×100 ml). The aqueous layer is concentrated in vacuo at room temperature.

The crude aqueous layer (876 g) may be used without further purification.

This aqueous solution contains felinine, sodium chloride, unreacted L-cysteine monochloride monohydrate and a trace quantity of 3-methyl-3-buten-1-ol; calculated quantity of felinine in solution is 0.119 g felinine equivalent to 1.09 g crude solution, (i.e. 10.92% felinine w/w).

Crude Solid

Reference may be made to "The Merck Index" Tenth Edition—Monograph 3883.

Synthesis of 3-mercapto-propan-1-ol

Preparation of mercaptans (thiols) can be achieved (1) by reacting an alkyl halide with thiourea to give an isothiourea hydrohalide, subsequent alkaline hydrolysis of this salt affords the mercaptan (thiol). The synthesis of 3-mercapto-propan-1-ol (2) is outlined in Scheme 1.

Scheme 1

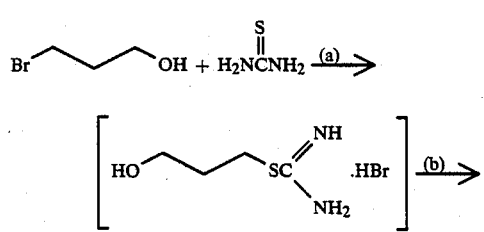

(a) 95% ethanol, 6 h reflux, 16 h room temperature
(b) 10% NaOH (aq), 3 h reflux.

Method

In a 100 ml round bottomed flask equipped with magnetic stirrer bar are placed 3-bromopropan-1-ol (5 g, 0.036 m) and 95% ethanol (25 ml) to this is added thiourea (2.7 g, 0.036 m) in one portion and the mixture heated to reflux for 6 hours, the mixture is allowed to cool to room temperature overnight. The solvent is removed in vacuo to afford the white crystalline isothiouronium bromide (7.7 g, 100%), to this added a 10% aqueous solution of sodium hydroxide (2.9 g, 0.072 m) and the mixture heated under reflux for 3 hours. The mixture is allowed to cool and the aqueous washed with dichloromethane (2×25 ml), the aqueous is then acidified with concentrated hydrochloric acid and extracted with dichloromethane (2×25 ml), dried over magnesium sulfate and concentrated in vacuo to afford a clear oil of crude 3-mercapto propan-1-ol 2.1 g (63%). GLC analysis showed this to be of 95% purity.

Distillation of the crude affords a clear oil with a boiling range of 75°–80° C. at 7 mm Hg pressure.

References

1. Fieser and Fieser Reagents for Organic Synthesis p. 1165 (Vol. 1).
2. Clinton et al. JACS 67, 594–7, 1945.

EXAMPLE I

Synthetic Blend

| Active Ingredients | % by weight |
|---|---|
| n-propanoic acid | 0.34 |
| 2-methyl propanoic acid | 2.57 |
| n-butanoic acid | 12.88 |
| 2-methyl butanoic acid | 40.91 |
| n-pentanoic acid | 1.97 |
| 4-methyl pentanoic acid | 7.59 |
| n-hexanoic acid | 1.59 |
| 2-phenyl ethanol | 0.26 |
| phenol | 5.98 |
| 2-piperidone | 0.50 |
| 4-methyl phenol | 2.01 |
| n-octanoic acid | 0.25 |
| n-decanoic acid | 0.32 |
| indole | 4.30 |
| n-dodecanoic acid | 0.20 |
| 3-phenyl propanoic acid | 14.20 |
| n-tetradecanoic acid (myristic acid) | 0.35 |
| oxindole | 0.30 |
| n-hexadecanoic acid | 1.74 |
| n-octadecanoic acid | 1.74 |
| | 100.00 |

The blend is based on Analysis I—acid extract of lion faeces.

2-piperidone may be substituted by 5-amino valeric acid.

| Ingredients | % by weight |
|---|---|
| Synthetic blend | 1.0 |
| Felinine (crude solid) | 0.2 |
| Freon (solvent) | 98.8 |

| Ingredients | % by weight |
|---|---|
| | 100.0 |

Weight ratio of felinine to saturated alkanoic acids: 0.28:1.

0.6 grams of the synthetic blend plus felinine was dissolved in 49.4 grams of Freon.

Deer were presented with food in buckets treated with the synthetic blend by spraying on the equivalent of 2 ml neat blend in the Freon solution; the deer were also presented with untreated food in other buckets; their behaviour was observed and recorded by video.

The deer showed signs of distress and a flight response away from the buckets containing the food with the synthetic blend. They showed no such response to the untreated food.

EXAMPLE II

Synthetic Blend

| Active Ingredients | % by weight |
|---|---|
| acetic acid | 0.93 |
| n-propanoic acid | 0.81 |
| 2-methyl propanoic acid | 0.31 |
| n-butanoic acid | 0.37 |
| 2-methyl butanoic acid | 0.18 |
| 3-methyl butanoic acid | 0.18 |
| 4-methyl pentanoic acid | 0.18 |
| phenyl acetic acid | 5.89 |
| 3-phenyl propanoic acid | 31.22 |
| p-hydroxy phenylacetic acid | 8.50 |
| 3-(p-hydroxyphenyl)propanoic acid | 51.43 |
| | 100.00 |

16 grams of this blend was dissolved in 500 ml diglyme.

The blend is based on published work on the acid constituents and proportions thereof in lion anal sac secretion (E. S. Albone et al.—"Life Sciences" Vol. 14 pp. 387–400 (1974)).

The blend was tested as in Example I except that instead of spraying the blend onto the food, a perforated plastic vessel filled with cotton wool was placed in the appropriate bucket with 2 ml of neat blend on the cotton wool. Similar results were obtained as in Example I. Synergistic results were obtainable with a composition also comprising felinine.

EXAMPLE III

Synthetic Blend

| Active Ingredients | % by weight |
|---|---|
| acetic acid | 4.00 |
| n-butanoic acid | 4.00 |
| 2-methyl propanoic acid | 6.00 |
| 3-methyl butanoic acid | 80.00 |
| trimethylamine | 6.00 |
| | 100.00 |

2.5 grams of this blend was dissolved in a solvent comprising 5 grams of propane diol.

This blend is based on the known constituents of fox urine.

The blend was tested as in Example II with similar results, with again improved results obtainable with a composition also comprising felinine.

EXAMPLE IV

Synthetic Blend

| Active Ingredients | % by weight |
|---|---|
| n-propanoic acid | 1.09 |
| 2-methyl propanoic acid | 3.99 |
| n-butanoic acid | 0.69 |
| 3-methyl butanoic acid | 41.12 |
| 2-methyl butanoic acid | 3.92 |
| n-pentanoic acid | 1.84 |
| 4-methyl pentanoic acid | 0.88 |
| n-hexanoic acid | 2.35 |
| n-heptanoic acid | 2.23 |
| n-octanoic acid | 3.71 |
| 4-methyl octanoic acid | 0.72 |
| n-nonanoic acid | 0.64 |
| n-nonanol | 0.40 |
| n-decanol | 4.78 |
| decan-2-ol | 0.66 |
| n-undecanol | 8.28 |
| n-dodecanol | 15.22 |
| n-tridecanol | 4.79 |
| n-tetradecanol | 2.06 |
| n-pentadecanol | 0.30 |
| n-hexadecanol | 0.33 |
| | 100.00 |

Weight ratio of $C_{14}$–$C_{16}$ saturated aliphatic alcohols to saturated alkanoic acids: 0.043:1.

This blend is based on Analysis II—Lions' anal sec secretion.

Synergistic results are obtainable when used with felinine.

EXAMPLE V

Synthetic Blend

| Active Ingredients | % by weight |
|---|---|
| n-propanoic acid | 1.286 |
| 2-methyl propanoic acid | 2.681 |
| n-butanoic acid | 5.685 |
| 2-methyl butanoic acid | 3.760 |
| 3-methyl butanoic acid | 3.688 |
| n-pentanoic acid | 0.486 |
| 4-methyl pentanoic acid | 0.450 |
| n-hexanoic acid | 0.414 |
| 2-methyl hexanoic acid | 0.126 |
| 2-phenylethanol | 0.207 |
| benzothiazole | 0.072 |
| n-heptanoic acid | 0.369 |
| phenol | 4.885 |
| 4-methyl phenol | 3.338 |
| 5-aminovaleric acid | 0.837 |
| 2-phenoxyethanol | 0.207 |
| n-octanoic acid | 0.414 |
| 4-methyl octanoic acid | 0.081 |
| n-nonanoic acid | 0.261 |
| 4-methyl nonanoic acid | 0.081 |
| n-tetradecanol | 0.090 |
| n-decanoic acid | 0.243 |
| n-pentadecanol | 0.369 |
| γ-decalactone | 0.108 |
| n-undecanoic acid | 0.171 |
| indole | 8.590 |
| n-hexadecanol | 0.504 |
| n-dodecanoic acid | 0.432 |
| phenyl acetic acid | 0.207 |
| 3-phenyl propanoic acid | 1.116 |
| n-tridecanoic acid | 0.153 |
| n-tetradecanoic acid (myristic acid) | 1.934 |
| oxindole | 1.529 |
| n-pentadecanoic acid | 0.126 |
| palmitic acid (n-hexadecanoic acid) | 11.721 |
| palmitoleic acid (cis-9-hexadecenoic acid) | 1.772 |
| stearic acid (n-octadecanoic acid) | 4.453 |
| oleic acid | 6.188 |

-continued

| Active Ingredients | % by weight |
|---|---|
| elaidic acid | 1.898 |
| linoleic acid | 3.409 |
| linolenic acid | 1.340 |
| arachidic acid (n-eicosanoic acid) | 0.225 |
| eicosenoic acid | 0.036 |
| 3$\beta$-cholestanol | 5.047 |
| cholesterol | 10.911 |
| pyrrolidine | 0.900 |
| piperidine | 0.900 |
| 2-pyrrolidone | 0.900 |
| 2-phenylethylamine | 0.900 |
| 3-methyl indole | 0.900 |
| diethylamine | 0.900 |
| n-propylamine | 0.900 |
| n-butylamine | 0.900 |
| 3-methyl butylamine | 0.900 |
| | 100.000 |

Weight ratio of $C_{14}$–$C_{16}$ saturated aliphatic alcohols to saturated alkanoic acids: 0.025:1.

Weight ratio of each of pyrrolidine, piperidine, 2-pyrrolidone, 2-phenyl ethylamine, 3-methyl indole, diethylamine, n-propylamine, n-butylamine and 3-methyl butylamine to saturated alkanoic acids: 0.023:1.

The blend was prepared by step-wise addition of components, followed by ultrasonic treatment to homogenize.

Composition

| Ingredients | grams | % by weight |
|---|---|---|
| Synthetic blend | .004 | 0.16 |
| Felinine | .034 | 1.38 |
| Bitrex | .002 | 0.08 |
| Primal AC-33 | 2.4 | 97.73 |
| Acetone (solvent) | .016 | 0.65 |
| | 2.456 | 100.00 |

Weight ratio of felinine to saturated alkanoic acids: 22:1.

The synthetic blend was first dissolved in the acetone with step-wise addition of the remaining components and vigorous manual shaking. The felinine was provided as 0.31 grams of the crude reaction mixture of felinine in water containing also sodium chloride, unreacted L-cysteine monochloride monohydrate and a trace quantity of 3-methyl-3-buten-1-ol. The Bitrex was provided as 0.78 ml of a 0.256% weight/volume solution.

The composition was dissolved in water to 50 ml giving a concentration of synthetic blend of 0.008% weight/volume synthetic blend and 0.068% weight/volume felinine.

The aqueous composition was sprayed onto dried lucerne pellets, which were then allowed to dry overnight; the solution was sprayed in the amount of 50 ml solution/2 kg lucerne pellets.

A regular rectangular pattern of 6 buckets was provided in a restricted outside pen with the buckets arranged in (plan view) three side-by-side pairs. Each bucket contained initially 2 kg. of dried lucerne pellets. One bucket of each pair contained the treated pellets, the other bucket of the pair containing untreated lucerne pellets acting as a control. The treated bucket of the middle pair was on the other side of the rectangle from the treated buckets of the other two pairs.

Five red deer were starved for 24 hours and then allowed into the pen with their movements being recorded on video camera. Every hour for 8 hours the buckets were weighed to establish the quantity of food consumed; water was available ad libitum. After 4 hours the position of the control bucket and treated bucket of each pair were reversed to counteract any positional bias.

The Table shows the percentage of the food consumed at hourly intervals.

TABLE

| | Pair 1 | | Pair 2 | | Pair 3 | |
|---|---|---|---|---|---|---|
| Time (hrs) | Control | Treatment | Control | Treatment | Control | Treatment |
| 0 | 0 | 0 | 0 | 0 | 0 | 0 |
| 1 | 41 | | 27½ | | 73½ | |
| 2 | 63 | | 29 | | 86 | |
| 3 | 84 | | 29 | | 95 | |
| 4 | 100 | | 29 | | 99 | |
| 5 | | | 94½ | | 100 | |
| 6 | | 0 | 100 | | | |
| 7 | | 8½ | | | | |
| 8 | 100 | 8½ | 100 | 0 | 100 | 0 |

The video observations showed the deer had a considerable aversion to the treated buckets.

Similar experiments with a 0.256% weight/volume Bitrex solution alone sprayed onto lucerne pellets in amounts of 0.8–39 ml per bucket resulted in 18–37% of the food in the treated buckets being consumed as compared with 43%–100% in the control buckets.

The deer were repeatedly tested as above with comparable results being obtained.

EXAMPLE VI

Synthetic Blend: as in Example V

Composition

| Ingredients | grams | % by weight |
|---|---|---|
| Synthetic blend | 0.50 | .78 |
| Felinine | 2.99 | 4.68 |
| Bitrex | 0.05 | 0.08 |
| Primal AC-33 | 58.60 | 91.68 |
| Acetone | 1.78 | 2.78 |
| | 63.92 | 100.00 |

Weight ratio of felinine to saturated alkanoic acids: 15:1.

The blend and composition were prepared substantially as in Example V. The felinine was provided as 27.4 grams of the crude reaction mixture. The Bitrex was provided as 19.5 ml of the 0.256% solution. The composition was dissolved in water to 1250 ml giving a concentration of 0.04% weight/volume synthetic blend and 0.24% weight/volume felinine.

When the 1250 ml of the aqueous composition is sprayed onto 25 Scots Pine saplings in a large relatively unrestricted wooded enclosure excellent deer repelling results may be observed; with no significant repellent effect when Primal is sprayed on alone in a control experiment.

EXAMPLE VII

The procedure of Example VI was followed using the aqueous composition of that Example with the addition of the product of fermenting 7 whole chicken's eggs which represents 35.9 eggs per gram of saturated alkanoic acids in the blend; the fermented egg was slurrified in a little water before blending in. Excellent deer repelling results may be observed, following spraying onto Scots Pine saplings as in Example VI.

We have found that for example red deer, Pere David deer and Sika deer were all effectively repelled by compositions embodying the invention.

It will be realized that any one of the active compounds described hereinbefore alone or in admixture with one or more of the other active compounds may have an animal repellent effect per se.

We wish to record our appreciation of the valuable contributions made by The Zoological Society of London in the provision of materials and test facilities, and the Forestry Commission at Alice Holt Lodge, Research Station, Farnham, England.

EXAMPLE VIII

The blend and composition of Example V were modified by the addition of the following components in amounts by weight based on 100 grams of the unmodified blend of Example V

|  | grams |
|---|---|
| 3-mercapto propan-1-ol | 0.015 |
| 3-(methylthio) propanol | 0.014 |
| dimethyl sulfide | 0.076 |
| dimethyl trisulfide | 0.051 |
| dimethyl tetrasulfide | 0.015 |
| n-(2-phenylethyl) acetamide | 0.009 |
| n-butyl-N—ethyl acetamide | 0.091 |

We claim:

1. A repellent composition comprising (a) a synthetic blend of saturated alkanoic acids having 3–20 carbon atoms and which is characteristic of the acid fraction obtained by a Soxhlet extraction of lion feces followed by separation into basic, neutral and acid fractions; and (b) felinine.

2. A repellent composition of claim 1 wherein said felinine consists essentially of L-felinine.

3. A repellent composition of claim 1 wherein the weight ratio of felinine to saturated alkanoic acids is in the range of from about 0.25:1 to about 30:1.

4. A repellent composition of claim 1 wherein the weight ratio of felinine to saturated alkanoic acids is in the range of from about 10:1 to about 25:1.

5. A composition of claim 1 additionally including a member selected from the group consisting of:
saturated aliphatic alcohols containing 6–18 carbon atoms;
aryl substituted saturated alkanoic acids; and
one or more of pyrrolidine, piperidine, 2-pyrrolidone, 2-phenyl ethylamine, 3-methyl indole, diethylamine, n-propylamine, n-butylamine, 3-methyl butylamine and mixtures thereof.

6. A repellent composition of claim 5 wherein the saturated aliphatic alcohols contain 14–16 carbon atoms.

7. A repellent composition of claim 6 wherein the weight ratio of $C_{14}$–$C_{16}$ saturated aliphatic alcohols to saturated alkanoic acids is in the range of about 0.02–0.05:1 and the weight ratio of each of pyrrolidine, piperidine, 2-pyrrolidone, 2-phenyl ethylamine, 3-methyl indole, diethylamine, n-propylamine, n-butylamine and 3-methyl butylamine which is present to saturated alkanoic acids is about 0.025:1.

8. A repellent composition of claim 1 wherein the alkanoic acids are selected from the group consisting of n-propanoic acid, 2-methyl propanoic acid, n-butanoic acid, 2-methyl butanoic acid, 3-methyl butanoic acid, n-pentanoic acid, 4-methyl pentanoic acid, n-hexanoic acid, 2-methyl hexanoic acid, n-heptanoic acid, n-octanoic acid, 4-methyl octanoic acid, n-nonanoic acid, 4-methyl nonanoic acid, n-decanoic acid, n-undecanoic acid, n-dodecanoic acid, n-tridecanoic acid, n-tetradecanoic acid (myristic acid), n-pentadecanoic acid, n-hexadecanoic acid (palmitic acid), n-octadecanoic acid (stearic acid), n-eicosanoic acid (arachidic acid) and mixtures thereof and additionally optionally including one or more of a member selected from the group consisting of n-tetradecanol, n-pentadecanol, n-hexadecanol, phenyl acetic acid, 3-phenyl propanoic acid, 2-phenyl ethanol, phenol, 5-amino-valeric acid, 4-methyl phenol, indole, oxindole, oleic acid, linoleic acid, cholesterol, benzothiazole, 2-phenoxyethanol, 4-decalactone, palmitoleic acid (cis-9-hexadecenoic acid), elaidic acid, linolenic acid, eicosenoic acid, and $3\beta$-cholestenol.

9. A repellent composition of claim 1 additionally including a member selected from the group consisting of 3-mercapto propanol, 3-(methylthio)propan-1-ol, dimethyl sulfide, dimethyl trisulfide, dimethyl tetrasulfide, N-(2-phenylethyl)acetamide, N-butyl-N-ethyl acetamide and mixtures thereof.

10. A method of repelling animals wherein a composition according to claim 1 is employed.

11. A method of claim 10 wherein said animals comprise deer.

12. A composition comprising a fermented egg product and a repellent composition according to claim 1.

13. A composition of claim 12 wherein said fermented egg product is prepared by fermenting whole chicken eggs.

14. A composition of claim 13 having about 35 eggs per gram of saturated alkanoic acids.

15. A composition of claim 1 additionally including an agent to impart a bitter flavor to the composition.

16. A composition of claim 15 wherein said bitter flavor-imparting agent is selected from the group consisting of brucine, quassin, sucrose octa-acetate, quinine, caffeine, tannin and dinatonium benzoate.

17. A composition of claim 15 wherein said bitter flavor-imparting agent comprises dinatonium benzoate present in an amount of up to 2%, by weight, of said composition.

18. A composition of claim 1 additionally including an agent to impart adhesive properties to the composition.

19. A composition of claim 18 wherein said adhesive-imparting agent comprises an adhesive acrylic emulsion.

20. A composition of claim 17 additionally including an adhesive-imparting agent comprising an adhesive acrylic emulsion.

* * * * *